United States Patent [19]

Durvasula

[11] Patent Number: 4,526,984
[45] Date of Patent: Jul. 2, 1985

[54] AUTOXIDATION OF ALKYL-SUBSTITUTED AROMATIC ETHERS

[75] Inventor: Visweswara R. Durvasula, Cheshire, Conn.

[73] Assignee: The Upjohn Company, Kalamazoo, Mich.

[21] Appl. No.: 665,905

[22] Filed: Oct. 29, 1984

[51] Int. Cl.³ ............................................ C07D 307/89
[52] U.S. Cl. ..................................... 549/241; 549/243
[58] Field of Search ................................. 549/241, 243

[56] References Cited

U.S. PATENT DOCUMENTS 2,833,816  5/1958  Saffer et al. ..................... 562/421 X
3,652,598  3/1972  Broadhead ......................... 549/242

OTHER PUBLICATIONS

Paparinska et al., Khim Tekhnol Khim 1974, 2, 86–97, (Chemical Abstracts, 82, 124995r, 1975).

Primary Examiner—Richard L. Raymond
Attorney, Agent, or Firm—L. R. Hattan; J. S. Rose

[57] ABSTRACT

A method is described for autoxidizing ortho-dialkyl substituted aromatic ethers directly to their corresponding carboxylic acid anhydrides. The method comprises autoxidizing the ethers in a first step in a solution of an aliphatic monocarboxylic acid having 2 to 8 carbon atoms to form a partially oxidized reaction mixture. The autoxidation of the partially oxidized mixture is continued in a second step after the addition of an anhydride of an aliphatic monocarboxylic acid having 3 to 8 carbon atoms and at a temperature of at least 130° C. to form said anhydrides.

The anhydrides are used in the preparation of organic high temperature polymers such as polyamideimides, polyimides, polyetherimides, and polyetherimideamides.

15 Claims, No Drawings

AUTOXIDATION OF ALKYL-SUBSTITUTED AROMATIC ETHERS

FIELD OF THE INVENTION

This invention relates to the autoxidation of ortho dialkyl substituted aromatic compounds and is more particularly concerned with the autoxidation of ortho dialkyl substituted aromatic ethers.

DESCRIPTION OF THE PRIOR ART

The autoxidation of dialkyl substituted aromatic compounds to carboxylic acid products in aliphatic carboxylic acid solutions using heavy metal oxidation catalysts and promoters is well known, for example, see U.S. Pat. No. 2,833,816. When the reference autoxidation procedure is employed with ortho dialkyl substituted aromatics the desired carboxylic acids are obtained in low yields only. The oxidation of the first alkyl group to the carboxylic group goes readily but the result is the deactivation of the adjacent alkyl group towards autoxidation.

An added complication arises with ortho dialkyl substituted aromatics when there are two or more such aromatic rings joined by a linking radical such as carbonyl, sulfonyl, or ether linkage. Generally speaking, there is an even greater tendency towards lower product yields when such compounds are subjected to prior art autoxidation procedures. For example, Broadhead in U.S. Pat. No. 3,652,598 discloses the oxidation of various 2,2',3,3'- and 3,3',4,4'-tetraalkyldiphenylmethanes to the corresponding tetracarboxylic acids. However, product mixtures are obtained which contain mono-, di-, tri-, and tetracarboxylic acids. Accordingly, the yield of desired tetracarboxylic acid product is low and its isolation and purification from the complex reaction mixtures becomes complicated.

Paparinska et al, Khim Tekhnol Khim 1974, 2, 86–97 (Chem. Abstracts 82, 124995 r, 1975) have reported the cobalt acetate-sodium bromide catalyzed autoxidation of 3,3',4,4'-tetramethyldiphenyl ether to the corresponding tetracarboxylic acid in only a 40 to 50 percent yield.

A novel process has been discovered whereby a particular group of ortho dialkyl substituted aromatic ether compounds can be autoxidized directly in high yields and excellent purity to their corresponding carboxylic acid anhydrides.

SUMMARY OF THE INVENTION

This invention comprises a method for converting an aromatic compound selected from the formulae consisting of

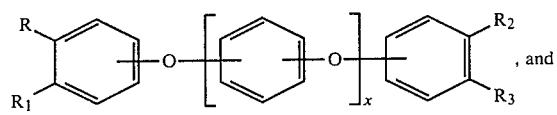

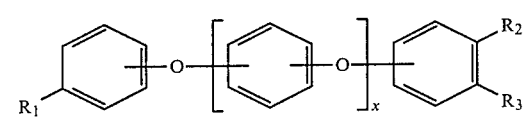

to the corresponding anhydrides having the formulae

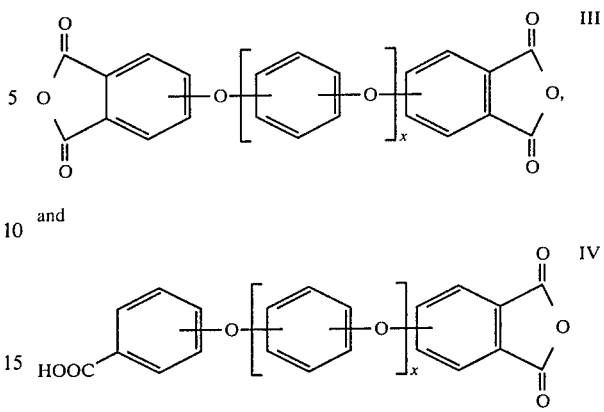

wherein $R$, $R_1$, $R_2$ and $R_3$ are independently selected from linear lower alkyl and x is 0, 1 or 2, said method comprising autoxidizing in a first step said aromatic compound in a solution comprising an aliphatic monocarboxylic acid having 2 to 8 carbon atoms with oxygen in the presence of a heavy metal oxidation catalyst and a promoter to form a partially oxidized reaction mixture, and in a second step adding an anhydride of an aliphatic monocarboxylic acid having 3 to 8 carbon atoms and continuing the autoxidation reaction at a temperature of at least 130° C. to form said anhydride.

The term "linear lower-alkyl" means alkyl having from 1 to 8 carbon atoms, inclusive, such as methyl, ethyl, propyl, butyl, amyl, hexyl, heptyl, and octyl.

The anhydrides (III) and anhydride-carboxylic acids (IV) obtained from the present method are used as intermediates in the preparation of various polymers but find their principal utility in the preparation of high temperature resistant polyamideimides, polyimides, polyetherimides and polyetherimideamides.

DETAILED DESCRIPTION OF THE INVENTION

The process in accordance with the present invention is characterized by certain novel aspects. First of all is the fact that the overall autoxidation is carried out in two distinct stages or steps in order to obtain the surprisingly high yields of the desired anhydrides. Second is the surprising fact that the ether oxygens on the aromatic rings enhance the reactivity in the overall process resulting in the direct formation of anhydride groups in high yields. Comparatively, when groups such as carbonyl, sulfonyl, and the like, link the aromatic rings carrying the ortho dialkyl groups the result is to retard the autoxidation process.

The first step of the autoxidation method in accordance with the present invention is carried out using procedures analogous to the prior art methods cited supra. That is to say, the compounds are autoxidized in a solution comprising an aliphatic monocarboxylic acid in the presence of any type of heavy metal oxidation catalyst known in the art and a promoter to form a partially oxidized reaction mixture. The reaction can be carried out in any suitable reaction vessel including glassware and sealed autoclaves capable of withstanding high pressures. For typical methods, including reaction procedures, oxidizing techniques including catalysts, promoters, and the like, the disclosure of U.S. Pat. No. 2,833,816 cited supra is incorporated herein by reference.

The term "partially oxidized reaction mixture" means a mixture of mono-, di-, tri-, and tetracarboxylic acids in varying proportions in the case of the starting compounds of formula (I); and a mixture of mono-, di-, and tricarboxylic acids in the case of compounds of formula (II). Generally speaking, the predominant components in both cases are the dicarboxylic acids with the fully oxidized products being present as minor constituents only.

The aliphatic monocarboxylic acid solvent employed in the first stage autoxidation is defined above as having 2 to 8 carbon atoms, and, preferably has 3 or 4 carbon atoms. Illustrative of these carboxylic acid solvents are acetic, propionic, butyric, isobutyric, valeric, caproic, heptylic, caprylic, and the like acids. Preferred are propionic, and butyric acids.

The concentration of starting compound in the carboxylic acid solvent is in no way critical being governed only by what is expedient. Advantageously, the compounds are present in acid solution in a concentration of from about 1 percent by weight to about 25 percent by weight.

The heavy metal oxidation catalyst can be used in its elemental finely divided form, or other combined forms. It has been found advantageous to employ the metals in the forms in which the metal ion itself is provided. Typical of the heavy metal catalysts are manganese acetate, cobalt acetate, nickel acetate, tin acetate, ammonium molybdate, cobalt hydroxy quinolate, and the like.

Preferred are the heavy metal acetates and particularly preferred is cobaltous acetate.

The amount of catalyst which is more efficacious can be easily determined by one skilled in the art. Advantageously, the catalyst is employed in an amount of from about 1 to about 20 mole percent based on moles of starting compound. Preferably, the catalyst is employed within a range of about 5 to about 15 mole percent.

Any of the known promoters which are found to increase the overall autoxidation rate can be used in the present process. Typical, but not limiting thereof, are methyl ethyl ketone, ozone, zirconyl acetate, sodium acetate, zinc acetate, sources of bromine such as hydrogen bromide, ammonium bromide, potassium bromate, tetrabromoethane, benzyl bromide, potassium bromide, sodium bromide, and the like. Preferred promoters are the compounds providing bromine, particularly ionic bromine, such as potassium bromide, sodium bromide, and the like.

The amount of promoter can vary within wide limits. For example, it can be used in an amount of from about 1 to about 15 mole percent based on the moles of starting aromatic compound.

In most cases it is advantageous to employ the catalyst and promoter in equimolar proportions.

The oxygen gas can be employed in the form of pure oxygen, or admixed with other inert gases including the use of air itself. Preferably, pure oxygen is used at a sufficient pressure to maintain a blanket of the gas above the reaction mixture.

The first stage autoxidation is advantageously carried out within a temperature range of from about 50° C. to about 250° C. Preferably, the temperature is from about 100° C. to about 150° C.

The time required to convert the starting compound to the partially oxidized reaction mixture defined above will vary depending on the aromatic compound, solvent, catalyst, temperature, and the like. Generally speaking, the first autoxidation stage is regarded as essentially complete when the reaction solution just becomes turbid or a slight precipitate forms.

Although not wishing the present invention to be bound by any theoretical considerations but only by the claims appended hereinbelow, it is believed that the turbidity formation represents a complex between the catalyst and a partially oxidized intermediate form of the starting material. The precipitation of this complex effectively stops any further progress of the autoxidation past the partially oxidized stage.

The second step of the autoxidation in accordance with the present invention involves the oxidation of the remaining linear alkyl groups which have resisted reaction in the first step and the formation of the anhydride groups. It is initiated by the addition of an anhydride of an aliphatic monocarboxylic acid having 3 to 8 carbon atoms to the partially oxidized reaction mixture and continuing the autoxidation at a temperature of at least 130° C. to form the desired products.

Preferred are the anhydrides having 3 or 4 carbon atoms.

Illustrative of the anhydrides are propionic anhydride, butyric anhydride, isobutyric anhydride, valeric anhydride, caproic anhydride, heptylic anhydride, caprylic anhydride, and the like. Preferred are propionic and butyric anhydrides.

In the event that acetic acid is used in the first stage autoxidation it is preferable that at least a portion of it be removed by distillation or the like from the partially oxidized reaction mixture prior to the addition of the anhydride. However, if the acid employed has a minimum of three carbon atoms then it can be left in the mixture during the second stage.

Accordingly, a preferred combination of acid and anhydride for use in the first and second stages is propionic acid and propionic anhydride respectively.

Although not essential, it is advantageous to employ the anhydride in at least molar equivalency for each equivalent of ortho-dialkyl groups present from (I) or (II). The equivalent weight of the ortho-dialkyl compounds is defined as the molecular weight divided by the number of pairs of ortho-alkyl groups contained therein. Preferably, the anhydride is employed in a 2 to 10 molar excess per equivalent of ortho-dialkyl groups.

In a preferred embodiment of the present method, the anhydride is added portionwise rather than all at once. This minimizes the formation of alkanoyloxyphthalide side-products which detract from the yield of the desired products.

The autoxidation is carried out under the same conditions as described for the first stage except that the temperature is at least about 130° C. as set forth above. Advantageously, the temperature is from about 130° to about 250° C., and, preferably 130° to 150° C.

As the autoxidation proceeds the reaction mixture becomes turbid as it does in the first stage. Addition of a fresh portion of anhydride removes the turbidity and the autoxidation proceeds further. Accordingly, the reaction is continued for the time required to effect the optimum conversion to the products.

The progress (of either the first or second stage autoxidations) can be followed using any convenient analytical technique such as thin layer chromatography (TLC), gas/liquid chromatography (GC), high pressure liquid chromatography (HPLC), and the like. TLC is a particularly useful means for following the course of the reaction and detecting the various components which may be present at any given stage.

The carboxylic acid anhydride products (III) and (IV) can be easily isolated from the reaction mixtures and obtained in pure form by known methods. Illustratively, the acid/anhydride solvent mixture can be removed by distillation procedures providing the products in crude form. The pure materials can be removed from the catalyst and promoter by extraction with an organic solvent followed by solvent removal.

A particularly efficacious means of product isolation comprises cooling the reaction solution to about 0° C. thereby causing the anhydrides to precipitate. The solid crystalline products are then isolated in high yields and a high state of purity simply by filtration methods and the like.

Preferred of the aromatic compounds defined above for autoxidation in accordance with the present method are those compounds (I) and (II) wherein the respective groupings of R, $R_1$, $R_2$, and $R_3$ and $R_1$, $R_2$, and $R_3$ are all methyl groups and preferred within these groupings are those compounds wherein x equals zero or 1.

Illustrative of the starting compounds are 3,3',4,4'-tetramethyldiphenyl ether, 3,3',4,4'-tetraethyldiphenyl ether, 3,3',4,4'-tetrapropyldiphenyl ether, 3,3',4,4'-tetrabutyldiphenyl ether, 3,3',4,4'-tetrahexyldiphenyl ether, 2,2',3,3'-tetramethyldiphenyl ether, 1,4-bis(3,4-dimethylphenoxy)benzene, 4,4'-bis(3,4-dimethylphenoxy)diphenyl ether, and the like; 3,4,4'-trimethyldiphenyl ether, 3,3',4-trimethyldiphenyl ether, 2,2',3-trimethyldiphenyl ether, 1-(3,4-dimethylphenoxy)-4-(4-methylphenoxy)benzene, 4-(3,4-dimethylphenoxy)-4'-(4-methylphenoxy)diphenyl ether, and the like.

Preferred species of the starting compounds are 3,3',4,4'-tetramethyldiphenyl ether, 4,4'-bis(3,4-dimethylphenoxy)diphenyl ether and 3,4,4'-trimethyldiphenyl ether.

The following examples describe the manner and process of making and using the invention and set forth the best mode contemplated by the inventor for carrying out the invention but are not to be construed as limiting.

EXAMPLE 1

The following experiment sets forth the preparation of 3,3',4,4'-diphenyl ether tetracarboxylic acid dianhydride in accordance with the present invention.

A 100 ml. three-necked flask was equipped with a stirrer, a thermometer, a reflux condenser, and a gas inlet tube (Pyrex, ASTM 40-60, 12 coarse). The flask was charged with 3.0 g. (0.0133 mole) of 99 percent plus pure 3,3',4,4'-tetramethyldiphenyl ether, 0.3 g. (0.0015 mole) of cobaltous acetate tetrahydrate, 0.15 g. (0.0015 mole) of sodium bromide, 0.4 g. of methyl ethyl ketone, and 35 ml. of propionic acid.

An oil bath controlled at 154° to 155° C. was placed under the flask and with oxygen flowing through the stirred solution at a rate of 200 ml. per minute the autoxidation was initiated. For the first 10 minutes the solution temperature remained at about 130° C. Over a 2.5 hour period the solution temperature dropped to about 125° C. (bath temp.=about 154°–155° C.) At the 5 hour mark the temperature remained at 125° C. Thin layer chromatography (TLC) of an aliquot sample which was spotted on a silica gel plate (5 cm×10 cm KF5 plate supplied by Whatman Filter Co., Clifton, N.J.) and developed with a 7/3 parts by weight solution of ethyl acetate/acetic acid showed the presence of di-, tri-, and tetracarboxylic acid components with the latter being only in minor amount. One and one-half hours later the temperature was still 125° C. (bath temp.=155° C.) and the solution was turbid. TLC analysis showed no change over the previous TLC.

A 5 ml. portion of propionic anhydride was added to the solution which caused it to clarify and the temperature increased to about 130° C. After about 1 hour a TLC analysis showed a product mix of some carboxylic acid component, a dianhydride, and a new component believed to be a phthalide propionate intermediate in minor amount. A half-hour later with a solution temperature of about 134° C., an additional 2.5 ml. of propionic anhydride was added and the autoxidation was continued overnight.

Approximately 24 hours after starting the reaction the temperature was 130° C. and TLC analysis showed the presence of only a dianhydride component. An additional 3.0 ml. of propionic anhydride was added to the solution.

The solution was cooled in a bath of ice-water whereupon a white solid precipitated. The solid was collected by suction filtration, washed with 5 to 10 ml. of fresh propionic acid and dried at 100° C. under 10 mm. of mercury pressure, wt.=2.6 g. (63.4% yield), m.p.=205°–210° C.

The filtrate was evaporated to dryness to provide a semi-solid residue to which there was added 5 ml. of propionic acid. A solid separated and was collected on a suction filter and dried, wt.=0.7 g., m.p.=205°–210° C.

TLC of an aliquot of the filtrate spotted and developed similarly to the TLC described above showed the presence of 3,3',4,4'-diphenyl ether tetracarboxylic acid dianhydride (compared to an authentic sample of the same dianhydride which was spotted next to the filtrate sample) and what was believed to be 5,5'-oxybis(3-propionoxyphthalide).

The filtrate was evaporated to dryness in a rotatory evaporator using water aspirator pressure to provide a crystalline residue, wt.=1.0 g. Proton nuclear magnetic resonance analysis showed the 1.0 g. solid residue was a 50/50 by weight mixture of the dianhydride product and the phthalide side product.

Thus there was prepared 3.8 g. (92% yield) of 3,3',4,4'-diphenyl ether tetracarboxylic acid dianhydride.

EXAMPLE 2

The following experiment sets forth the preparation of 1,4-bis(3,4-dicarboxyphenoxy)benzene dianhydride in accordance with the present invention.

Using the apparatus and general procedure set forth in Example 1, a 100 ml. reaction flask was charged with 3.1 g. (0.01 mole) of 1,4-bis(3,4-dimethylphenoxy)benzene, 0.2 g. (0.001 mole) of cobaltous acetate tetrahydrate, 0.1 (0.001 mole) of sodium bromide, 0.25 g. of methyl ethyl ketone, and 50 ml. of propionic acid.

After running the autoxidation for about 16.5 hours at a bath temperature of 150° to 160° C. and reaction solution temperature of 130° C. under a 200 ml./minute flow of oxygen, a solid precipitated. TLC analysis of the solid dissolved in ethyl acetate for spotting on the TLC plate showed a mixture of dicarboxylic acid product, tricarboxylic acid product, and dianhydride.

A 5 ml. portion of propionic anhydride was added to the reaction solution dissolving the precipitate and the autoxidation continued for about 4 hours at a solution temperature of about 130° C. TLC analysis showed a trace of tetracid, a trace of what was believed to be the diphthalide derivative of the starting compound, and the major constituent of the dianhydride. Continuation of the autoxidation for a further 2.5 hour period resulted in the complete absence of tetracid by TLC analysis.

The reaction solution was allowed to stand overnight at room temperature causing the precipitation of solid dianhydride. The solid was collected on a suction filter, washed with excess fresh propionic acid and dried under a vacuum of 10 mm of mercury; wt.=2.4 g., m.p. 260°–262° C. The filtrate contained an additional amount of the dianhydride product which was not isolated.

Thus there was prepared at least a 60 percent isolated yield of the dianhydride product.

EXAMPLE 3

The following experiment sets forth the preparation of 4-(4'-carboxyphenoxy)phthalic anhydride in accordance with the present invention.

Using the apparatus and general procedure set forth above in the previous examples, a 500 ml. reaction flask was charged with 21.2 g. (0.1 mole) of 3,4,4'-trimethyldiphenyl ether, 1.6 g. (0.008 mole) of cobaltous acetate tetrahydrate, 0.8 g. (0.008 mole) of sodium bromide, 2.0 g. of methyl ethyl ketone, and 160 ml. of propionic acid.

The flask was heated in an oil bath at 150° to 155° C. while oxygen was bubbled into the stirred solution at a rate of 200 ml./minute. The solution temperature quickly reached 130° C. After 4 hours the reaction temperature had dropped to 116° C. and the solution had become turbid. TLC analysis using two different developing solutions of ethyl acetate/propionic acid in the weight ratios of 55/1 and 9/1 showed that the reaction solution contained predominantly the intermediate diacid (verified with the 55/1 developing solution) and the other constituent being the triacid (verified by the 9/1 solvent).

To the reaction mixture there was added 40 ml. of propionic anhydride which clarified the solution and caused the temperature to rise to 130° to 134° C. After about one hour the solution turned turbid again and the temperature dropped to 125° to 127° C. A 25 ml. portion of propionic anhydride was added clarifying the solution. The oxygen flow was reduced whereupon the temperature reached 135° C. and after 1.5 hours another 5 ml. of propionic anhydride was added. After about 30 minutes, the autoxidation was stopped and the clear solution cooled in an ice-water bath. The solid product precipitated almost immediately and was allowed to stand overnight.

The product was collected on a suction filter, washed with about 50 ml. of propionic acid, air dried followed by drying in a vacuum oven (about 10 mm. of mercury pressure) at 100° C. for 2 hours; wt.=22.5 g., m.p. 235°–238° C. The filtrate contained an additional amount of product which was not isolated.

Thus there was prepared at least a 79 percent isolated yield of the anhydride product.

I claim:

1. A method for converting an aromatic compound selected from the formulae consisting of

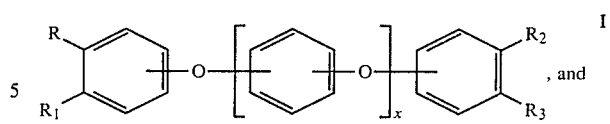

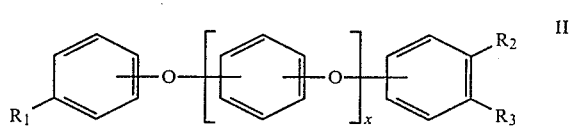

to the corresponding anhydrides having the formulae

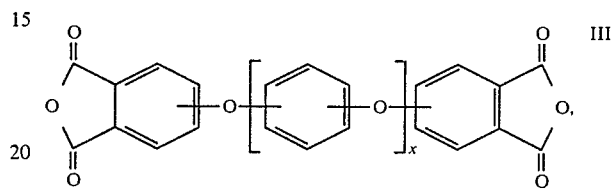

and

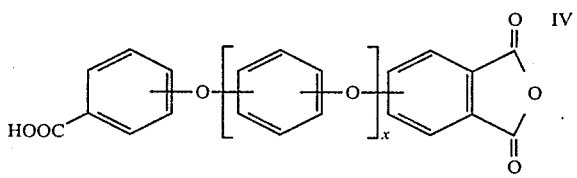

wherein R, $R_1$, $R_2$, and $R_3$ are independently selected from linear lower alkyl and x is 0, 1, or 2, said method comprising autoxidizing in a first step said aromatic compound in a solution comprising an aliphatic monocarboxylic acid having 2 to 8 carbon atoms with oxygen in the presence of a heavy metal oxidation catalyst and a promoter to form a partially oxidized reaction mixture, and in a second step adding an anhydride of an aliphatic monocarboxylic acid having 3 to 8 carbon atoms, and continuing the autoxidation reaction at a temperature of at least 130° C. to form said anhydride.

2. A method according to claim 1 wherein said monocarboxylic acid and anhydride are propionic acid and propionic anhydride, respectively.

3. A method according to claim 1 wherein said catalyst and promoter are cobaltous acetate and sodium bromide, respectively.

4. A method according to claim 1 wherein said second autoxidation step is carried out at a temperature of from about 130° C. to about 250° C.

5. A method according to claim 1 wherein said aromatic compound (I) is converted to said anhydride (III).

6. A method according to claim 5 wherein R, $R_1$, $R_2$, and $R_3$ in (I) are all methyl groups.

7. A method according to claim 6 wherein 3,3',4,4'-tetramethyldiphenyl ether is converted to 3,3',4,4'-diphenylether tetracarboxylic acid dianhydride.

8. A method according to claim 6 wherein 1,4-bis(3,4-dimethylphenoxy)benzene is converted to 1,4-bis(3,4-dicarboxyphenoxy)benzene dianhydride.

9. A method according to claim 1 wherein said aromatic compound (II) is converted to said anhydride (IV).

10. A method according to claim 9 wherein $R_1$, $R_2$, and $R_3$ in (II) are all methyl groups.

11. A method according to claim 10 wherein 3,4,4'-trimethyldiphenyl ether is converted to 4-(4'-carboxyphenoxy)phthalic anhydride.

12. A method according to claim 1 comprising autoxidizing in a first step said aromatic compound with oxygen in the presence of cobaltous acetate catalyst and sodium bromide promoter in a solution comprising propionic acid to form a partially oxidized reaction mixture and in a second step adding propionic anhydride and continuing the autoxidation reaction at a temperature of about 130° to about 250° C. to form said anhydride.

13. A method according to claim 12 wherein 3,3',4,4'-tetramethyldiphenyl ether is converted to 3,3',4,4'-diphenylether tetracarboxylic acid dianhydride.

14. A method according to claim 12 wherein 1,4-bis(3,4-dimethylphenoxy)benzene is converted to 1,4-bis(3,4-dicarboxyphenoxy)benzene dianhydride.

15. A method according to claim 12 wherein 3,4,4'-trimethyldiphenyl ether is converted to 4-(4'-carboxyphenoxy)phthalic anhydride.

* * * * *